US010916342B2

United States Patent
Vilnai et al.

(10) Patent No.: US 10,916,342 B2
(45) Date of Patent: Feb. 9, 2021

(54) SYSTEMS AND METHODS FOR ANALYZING NETWORK PACKETS

(71) Applicant: Cynerio Israel Ltd., Ramat Gan (IL)

(72) Inventors: Roey Vilnai, Tel-Aviv (IL); Daniel Brodie, Rehovot (IL); Leon Lerman, Ashdod (IL)

(73) Assignee: Cynerio Israel Ltd., Ramat Gan (IL)

( * ) Notice: Subject to any disclaimer, the term of this patent is extended or adjusted under 35 U.S.C. 154(b) by 0 days.

(21) Appl. No.: 16/413,671

(22) Filed: May 16, 2019

(65) Prior Publication Data

US 2020/0365252 A1     Nov. 19, 2020

(51) Int. Cl.
*G16H 30/20* (2018.01)
*H04L 12/26* (2006.01)
*G06F 16/51* (2019.01)

(52) U.S. Cl.
CPC ............. *G16H 30/20* (2018.01); *G06F 16/51* (2019.01); *H04L 43/04* (2013.01); *H04L 43/065* (2013.01)

(58) Field of Classification Search
CPC .............................. H04L 43/065; H04L 43/04
See application file for complete search history.

(56) References Cited

U.S. PATENT DOCUMENTS

| | | | |
|---|---|---|---|
| 6,574,629 B1* | 6/2003 | Cooke, Jr. | G06F 16/40 |
| 8,418,249 B1* | 4/2013 | Nucci | G06F 21/552 706/20 |
| 2005/0207658 A1* | 9/2005 | Schofield | H04L 69/04 382/232 |
| 2011/0317892 A1* | 12/2011 | Greenspan | A61B 6/5217 382/128 |
| 2014/0330855 A1* | 11/2014 | Atanasiu | G06F 19/321 707/759 |
| 2020/0097589 A1* | 3/2020 | Fu | G06F 17/18 |

* cited by examiner

*Primary Examiner* — Brenda H Pham

(57) ABSTRACT

There is provided a system for computing connectivity of medical imaging network nodes, comprising: at least one hardware processor executing a code for: monitoring packets transmitted over a network connecting a plurality of network nodes, analyzing the monitored packets to identify packets associated with a Digital Imaging and Communications in Medicine (DICOM) protocol, analyzing the packets associated with the DICOM protocol to identify medical imaging network nodes implementing the DICOM protocol, designating a respective medical imaging type for each node of the medical imaging network nodes, and computing a data structure storing connectivity of the medical imaging network nodes each designated with the respective medical imaging type.

28 Claims, 8 Drawing Sheets

SYSTEMS AND METHODS FOR ANALYZING NETWORK PACKETS

FIELD AND BACKGROUND OF THE INVENTION

The present invention, in some embodiments thereof, relates to analysis of packets and, more specifically, but not exclusively, to analysis of packets associated with nodes implementing a Digital Imaging and Communications in Medicine (DICOM)® protocol.

DICOM® is the international standard to transmit, store, retrieve, print, process, and display medical imaging information. DICOM® makes medical imaging information interoperable, and integrates image-acquisition devices, PACS, workstations, VNAs and printers from different manufacturers (https://www(dot)dicomstandard(dot)org/).

SUMMARY OF THE INVENTION

According to a first aspect, a system for computing connectivity of medical imaging network nodes, comprises: at least one hardware processor executing a code for: monitoring packets transmitted over a network connecting a plurality of network nodes, analyzing the monitored packets to identify packets associated with a Digital Imaging and Communications in Medicine (DICOM) protocol, analyzing the packets associated with the DICOM protocol to identify medical imaging network nodes implementing the DICOM protocol, designating a respective medical imaging type for each node of the medical imaging network nodes, and computing a data structure storing connectivity of the medical imaging network nodes each designated with the respective medical imaging type.

According to a second aspect, a method of computing connectivity of medical imaging network nodes, comprises: monitoring packets transmitted over a network connecting a plurality of network nodes, analyzing the monitored packets to identify packets associated with a Digital Imaging and Communications in Medicine (DICOM) protocol, analyzing the packets associated with the DICOM protocol to identify medical imaging network nodes implementing the DICOM protocol, designating a respective imaging type for each node of the medical imaging network nodes, and computing a data structure storing connectivity of the medical imaging network nodes each designated with the respective imaging type.

According to a third aspect, a computer program product for computing connectivity of medical imaging network nodes, comprises: a non-transitory memory storing thereon code for execution by at least one hardware process, the code including instructions for: monitoring packets transmitted over a network connecting a plurality of network nodes, analyzing the monitored packets to identify packets associated with a Digital Imaging and Communications in Medicine (DICOM) protocol, analyzing the packets associated with the DICOM protocol to identify medical imaging network nodes implementing the DICOM protocol, designating a respective imaging type for each node of the medical imaging network nodes, and computing a data structure storing connectivity of the medical imaging network nodes each designated with the respective imaging type.

In a further implementation of the first, second, and third aspects, further comprising code for monitoring for changes to the data structure.

In a further implementation of the first, second, and third aspects, the data structure is used as a behavioral model, and wherein the monitoring for changes to the data structure comprises iterating the monitoring packets, the analyzing the monitored packets, the analyzing the packets associated with the DICOM protocol, the designating the respective medical imaging type, and wherein computing comprises an update of the data structure, and comparing the update of the data structure to the behavioral model.

In a further implementation of the first, second, and third aspects, further comprising code for analyzing the monitored changes to the data structure to identify likelihood of at least one of: an anomaly, malicious activity, malware, addition of a new medical imaging network node, and removal of an existing medical imaging network node.

In a further implementation of the first, second, and third aspects, further comprising generating instructions for containing or removing or preventing damage from or fixing damage due to the at least one of: an anomaly, malicious activity, malware, addition of a new medical imaging network node, and removal of an existing medical imaging network node.

In a further implementation of the first, second, and third aspects, further comprising code for: designating each identified medical imaging network node as a medical imaging server or a medical imaging client, analyzing the packets associated with DICOM data to identify direction of flow of traffic and between identified medical imaging servers and medical imaging clients, and mapping identified medical imaging servers and medical imaging clients according to the identified direction of flow of traffic, wherein the data structure stores the identified medical imaging servers and medical imaging clients according to the identified direction of traffic flow.

In a further implementation of the first, second, and third aspects, further comprising code for determining at least one network port for each respective medical imaging server and storing the determined at least one network port in association with each respective medical imaging server, and code for determining a name of an imaging entity for each respective medical imaging client and storing the determined name of the imaging entity in association with each respective medical imaging client.

In a further implementation of the first, second, and third aspects, further comprising code for: designating the respective medical imaging type for each node of a sub-set of the identified medical imaging network nodes according to a mapping dataset, wherein another sub-set of the identified medical imaging network nodes are undesignated with medical imaging type, and classifying, by a a classifier, at least one node of the another sub-set of undesignated medical imaging nodes, into a respective medical imaging type, creating an updated sub-set of identified medical imaging network nodes by including the classified medical imaging type of each node classified by the classifier, and iterating the classifying and the creating, by feeding the updated sub-set of identified medical imaging network nodes and associated features dynamically extracted from packets associated with each respective classified node, obtained during a previous iteration, into the classifier during a current iteration, until a stop condition is met.

In a further implementation of the first, second, and third aspects, the classifier is trained according to a training dataset including tags indicative of a medical imaging type of each node of identified medical imaging nodes and associated features extracted from packets associated with each respective medical imaging network node.

In a further implementation of the first, second, and third aspects, the mapping dataset maps between at least one static signature extracted from a respective packet and one of a plurality of medical imaging types.

In a further implementation of the first, second, and third aspects, the static signature includes at least one of: DICOM implementation UID and DICOM implementation version name.

In a further implementation of the first, second, and third aspects, the associated features include at least one of: local features of the respective node independent of medical imaging types of neighboring nodes, and relational features dependent on medical imaging types of neighboring nodes.

In a further implementation of the first, second, and third aspects, the local features include at least one of: overall number of C-STORE messages sent by the respective node, and overall number of other nodes with which the respective node communicates with, wherein the relational features include at least one of: number of C-STORE messages sent by the respective node to a PACS.

In a further implementation of the first, second, and third aspects, the associated features are dynamically extracted according to packets captured by a sliding window defining a time interval.

In a further implementation of the first, second, and third aspects, the medical imaging type of at least one of the medical imaging network nodes is a medical imaging modality, and further comprising code for: extracting at least one feature from packets associated with each respective medical imaging network node designated and/or classified as medical imaging modality, classifying the at least one feature by another classifier, into a medical imaging modality sub-type of a plurality of medical imaging modality sub-types, and designating each respective medical imaging network node classified and/or designated as medical imaging type into the classified medical imaging modality sub-type.

In a further implementation of the first, second, and third aspects, the at least one feature includes DICOM SOP classes.

In a further implementation of the first, second, and third aspects, the analyzing the monitored packets to identify packets associated with the DICOM protocol comprises classifying the monitored packets by a hierarchical classifier comprising a plurality of sub-classifiers arranged in a sequence, wherein output of one sub-classifier earlier in the sequence is provided as input into another sub-classifier later on in the sequence.

In a further implementation of the first, second, and third aspects, a first sub-classifier of the sequence is trained on a first training dataset of packets each labeled with an indication of DICOM data or no DICOM data, wherein the distribution of the packets of the first training dataset is based on historical actual distribution of packets associated with DICOM data with respect to other packets not associated with DICOM data for a plurality of sample networks including imaging nodes.

In a further implementation of the first, second, and third aspects, the percentage of packets labeled with the indication of DICOM data in the first training set is about 0.5%-1.0%.

In a further implementation of the first, second, and third aspects, a second sub-classifier of the sequence following the first sub-classifier is trained on a second training dataset wherein a percentage of packets associated with DICOM data is higher than the percentage of packets associated with DICOM data of the first training dataset.

In a further implementation of the first, second, and third aspects, the percentage of packets labeled with the indication of DICOM data in the second training set is about 50%-90%.

In a further implementation of the first, second, and third aspects, for a plurality of sub-classifiers of the hierarchical classifier, each sub-classifier of the sequence is trained on a training dataset wherein a percentage of packets associated with DICOM data is higher than the percentage of packets associated with DICOM data of a training dataset used to train the previous sub-classifier of the sequence.

In a further implementation of the first, second, and third aspects, each sub-classifier is implemented as a logistic regression classifier.

In a further implementation of the first, second, and third aspects, the hierarchical classifier is distributed across a plurality of computing nodes for real time computation of a large volume of packets.

In a further implementation of the first, second, and third aspects, the hierarchical classifier classifies each packet based on a plurality of extracted features, including: byte distribution, payload size, and interval between packets.

In a further implementation of the first, second, and third aspects, the data structure is a directed graph, wherein nodes of the directed graph denote medical imaging nodes including medical imaging servers and medical imaging clients, and directed edges between nodes of the directed graph denote direction of traffic.

In a further implementation of the first, second, and third aspects, the monitoring packets is performed by a packet monitoring device that centrally monitors all packets flowing in the network.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF SPECIFIC EMBODIMENTS OF THE INVENTION

Figure 1:
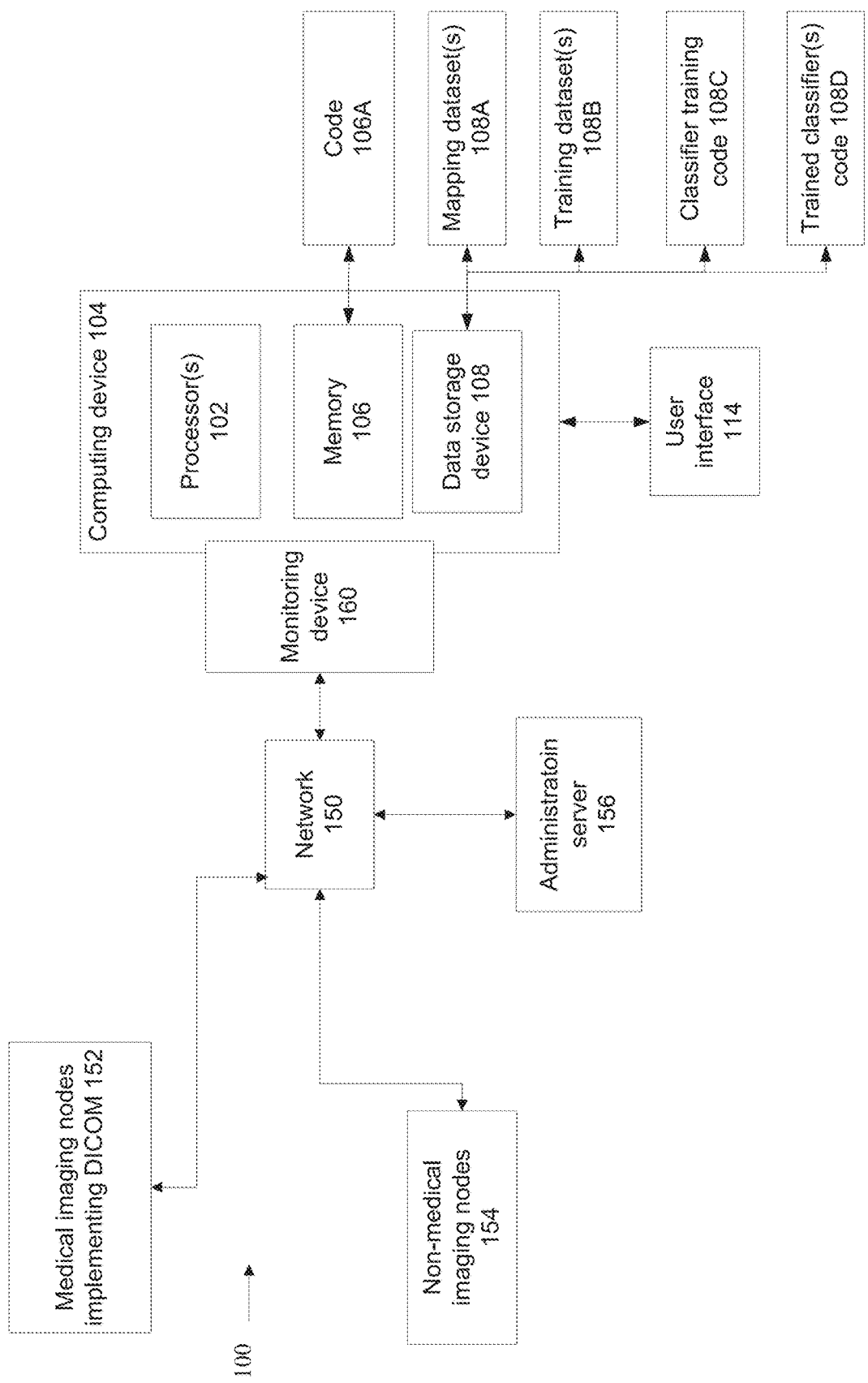
FIG. 1 is a schematic of components of a system for computing connectivity of network connecting imaging devices, in accordance with some embodiments of the present invention.

The present invention, in some embodiments thereof, relates to analysis of packets and, more specifically, but not exclusively, to analysis of packets associated with nodes implementing a Digital Imaging and Communications in Medicine (DICOM)® protocol.

An aspect of some embodiments of the present invention relates to systems, methods, an apparatus, and/or code instructions for computing connectivity of medical imaging nodes. Packets transmitted over a network are monitored. The network includes multiple nodes, some of which are related to medical imaging, and some of which are not related to medical imaging. The packets are analyzed to identify packets associated with DICOM®. The packets identified as associated with DICOM® are analyzed to identify medical imaging network nodes. A respective medical imaging type is designated for each of the identified medical imaging network nodes. A data structure, optionally a dependency graph, is computed. The data structure stores connectivity of the identified medical imaging nodes, each designated with respective medical imaging type. Also, the data structure defines relationships between clients, and servers. For example, PACS, client terminals accessing the PACS to view images, CT machines, MRI machines, x-ray machines, and ultrasound machines.

Once connectivity is known, the connectivity may be monitored to detect anomalies in the connectivity, indicative of, for example, malicious activity, malware, anomaly, removal of existing nodes (e.g., theft, error, reset, discontinuation, movement to another location), and/or addition of new nodes (e.g., authorized nodes, unauthorized nodes performing malicious activity, node moved from another location, new device being added). Instructions may be generated in response, for example, executing anti-malware applications, isolating a suspicious node, and automatically adding a new authorized node to access electronic medical records.

Optionally, the monitored packets are analyzed to identify packets associated with DICOM® by a hierarchical classifier, where outputs of one classifier is fed into another classifier. Each classifier is trained using a different training dataset having increasingly higher percentage of DICOM® packets.

Optionally, the respective medical imaging type of identified medical imaging nodes is first performed using a mapping dataset, optionally based on static signatures. A sub-set of identified medical imaging nodes remain undesignated. Features extracted for nodes of the undesignated sub-set are iteratively fed into a classifier. In each iteration, some nodes are designated, and some nodes remain undesignated. During the next iteration, features extracted from the nodes designated during the previous iteration(s) are fed into the classifier for classification of the remaining undesignated nodes, until a stop condition is met, for example, all nodes are designated and/or no changes have occurred between iterations.

At least some implementations of the systems, apparatus, methods, and/or code instructions described herein improve the technology of automated network mapping, by automatically identifying medical imaging network nodes (e.g., medical imaging devices, PACS server, radiology workstation, client terminal for accessing and presenting medical images) that implement the DICOM® protocol. In particular, performing the automated network mapping of nodes implementing the DICOM® protocol from an analysis of packets transmitted over the network, without necessarily accessing and/or querying the nodes themselves. For example, imaging departments in hospitals and other healthcare facilities are among the most network-connected departments. These departments consist of a wide variety of devices, servers, workstations and other endpoints that are designed specifically for the medical imaging world. No technology exists for automatically creating a network map (e.g., graph) of the medical imaging nodes implementing the DICOM® protocol, most likely as a result of a lack of a defined way for identifying packets associated with the DICOM® protocol. The technical problem of automated network mapping of medical imaging network nodes that implement the DICOM® protocol is especially challenging in view of the many different communication protocols implements for network communication. Moreover, the imaging departments may include network nodes that do not implement the DICOM® protocol (e.g., client terminal of an administrative assistant), which are difficult to distinguish from the nodes that do implement the DICOM® protocol, since the DICOM® protocol is not a communication protocol. At least some implementations of the systems, apparatus, methods, and/or code instructions described herein automatically identify medical imaging network nodes implementing the DICOM® protocol by analyzing packets transmitted across the network, optionally at a central location, without necessarily installing additional code at the end medical imaging nodes and/or without necessarily accessing the end nodes to query data at the end nodes (e.g., without detecting DICOM® software installation at the end nodes, and/or without obtaining the network configuration from the end node).

At least some implementations of the systems, apparatus, methods, and/or code instructions described herein address the technical problem of creating a data structure (e.g., graph) of medical imaging network nodes that implement the DICOM® protocol. The DICOM® protocol is not only a communication protocol, creating a technical challenge in identifying network nodes that do implement the DICOM® protocol from packet transmitted across the network, without necessarily querying the network nodes. For example, in contrast to standard network communication protocols which can be easily identified by a value in a predefined field of a packet format, packet carrying imaging data defined by the DICOM® protocol cannot easily be identified since no predefined field is defined by the communication protocol indicating the presence of DICOM® payload. At least some implementations of the systems, apparatus, methods, and/or code instructions described herein provide the technical solution of analyzing the packets to identify packets associated with DICOM®, identifying medical imaging network nodes implementing the DICOM® from the packets, and computing the connectivity of the medical imaging nodes implementing the DICOM® protocol.

At least some implementations of the systems, apparatus, methods, and/or code instructions described herein improve the technology of security medical imaging network nodes (that implement the DICOM® protocol), in particular providing real time security. For example, against malicious attack (e.g., by malware and/or by a malicious human entity), against malicious actions, against anomalies (e.g., errors not necessarily due to malicious intent, against theft of medical imaging devices, and/or against incorrect installation of new medical imaging devices. The data structure (e.g., graph) defining connectivity of the medical imaging nodes is created as described herein, and defines a behavioral model of medical imaging nodes. Packets of the network are monitored, and anomalies from the model are identified. These anomalies may indicate a possible security issue, and may trigger generation of instructions to deal with the security issue. For example, a removal of an existing medical imaging node from the connectivity graph may indicated a problem, for example, physical theft of the medical imaging device, anomalous behavior of the medical imaging device (e.g., error in operation), and/or a malware attack on the medical imaging device. In another example, a change in the status of a certain node from client to server may indicate a possible security breach in which the data is being stolen from the PACS server.

At least some implementations of the systems, apparatus, methods, and/or code instructions described herein improve the technology of analyzing a large rate of transmitted packets (i.e., large number of packets over a limited time interval) to identify the medical imaging nodes, accurately and/or in a computationally efficient manner. Moreover, the distribution of DICOM® related packets is very small, about 0.5-1.0%, increasing the technical challenge of correctly picking out the DICOM® related packets from the rest of the packet traffic. The hierarchical classifier described herein, is designed to process large volumes of packet traffic, and provide accurate real time classification, by classifying each packet as being associated with the DICOM® protocol or not. The first level classifier is designed to process the large rate of transmitted packets in real time to pick out the relatively small number of packets most likely to be associated with the DICOM® protocol. The first level classifier may be designed to have high recall, but at the cost of relatively low precision and/or relatively high false positive rate. The precision may be relatively low due to the low percentage of DICOM® associated packets relative to total packet traffic. The first level classifier is trained to accurately capture a large percentage of packets associate with DICOM® protocol, at the cost of incorrectly identifying packets which are not associated with DICOM® protocol. The second and higher level classifier(s) are designed and/or trained to sort through the packets classified as associated with the DICOM® protocol to more accurately distinguish which packets are actually associate with the DICOM® protocol from the packets incorrectly classified as being associated with the DICOM® protocol by the first level classifier. Moreover, the hierarchical classifier may be distributed, improving real time classification ability.

At least some implementations of the systems, apparatus, methods, and/or code instructions described herein address the technical problem of identifying an imaging type of the identified imaging nodes. Such imaging types are not defined by the DICOM® protocol. The technical problem may arise since in practice, medical imaging nodes may not identify themselves, making the identifying of their imaging type challenging. For example, the imaging type cannot be directly inferred by an analysis of static data of the packet. At least some implementations of the systems, apparatus, methods, and/or code instructions described herein provide a technical solution, by iteratively using a classifier on the medical imaging nodes for which the imaging type is discernible in association with medical imaging nodes for which the imaging type has been determined. The trained classifier is iteratively applied to the nodes which were previously not classified into imaging types. Feature are extracted from those nodes which were successfully classified by the classifier in a previous iteration(s) for classifying additional nodes during a current iteration. During each iteration additional unclassified nodes are classified, and/or previously classified nodes are re-classified. The process is iterated until a stop condition is met, for example, all nodes are classified by the classifier into imaging types. For example, once a PACS server is identified, then during the next iteration, nodes sending packets to the PACS are identified as imaging modalities.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
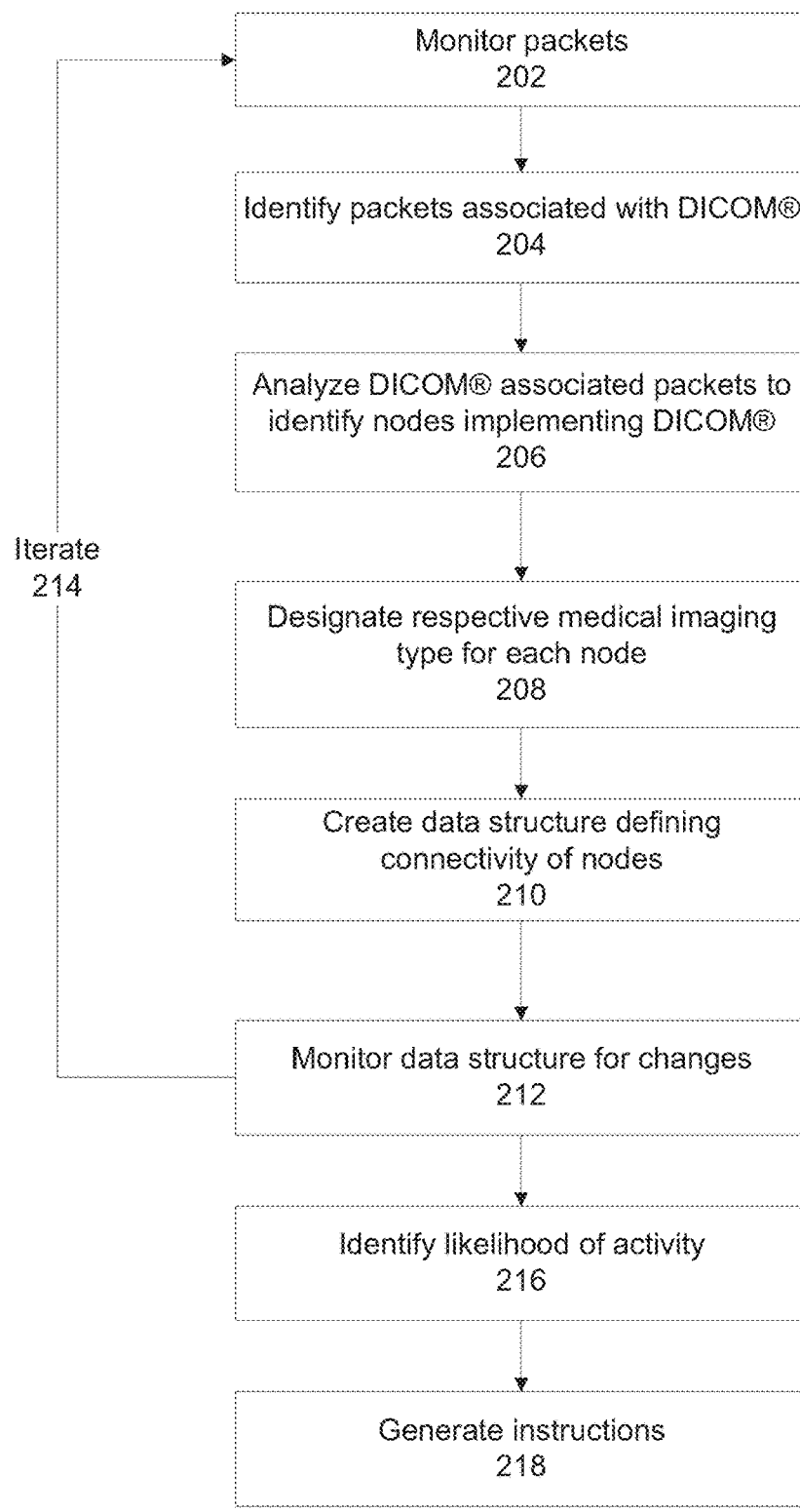
FIG. 2 is a flowchart of a method of computing connectivity of network connecting imaging devices, in accordance with some embodiments of the present invention.

Reference is now made to FIG. 1, which is a schematic of components of a system 100 for computing connectivity of network connecting imaging devices, in accordance with some embodiments of the present invention. Reference is also made to FIG. 2, which is a flowchart of a method of computing connectivity of network connecting imaging devices, in accordance with some embodiments of the present invention. System 100 may implement the acts of the method described with reference to FIGS. 2-3, by processor (s) 102 of a computing device 104 executing code instructions (e.g., code 106A) stored in a memory (also referred to as a program store).

Computing device 104 monitors packets transmitted over a network 150 by medical imaging network nodes that implement DICOM 152, and by other network nodes 154. Nodes 152 are automatically identified based on an analysis of the monitored packets performed by computing device 104, as described herein. The connectivity of nodes 152 is automatically computed by computing device 104, as described herein. The connectivity of the nodes may be monitored to detect changes, which may be transmitted to an administration server 156, which may generated instructions accordingly, as described herein.

Exemplary medical imaging network nodes that implement DICOM 152 include: PACS server, radiology workstations for viewing medical images, and/or imaging modality devices that capture medical images (e.g., ultrasound, CT, MRI, mammography device, x-ray device, nuclear medicine device).

Exemplary other network nodes 154 include other network connected devices, for example, client terminals of patients, printers, fax machines, etc.

Administration server 156 may include, for example, a security server for handling malicious activity, anomalies, and/or malware, for example, by executing anti-malware code, isolating suspicious devices from the network, and/or preventing further malicious behavior by removing accounts of users suspected of malicious activity.

Computing device 104 is programmed and/or positioned within network 150 to monitor and/or intercept packets transmitted over network 150 by nodes 152 and/or 154. Computing device 104 may be located within a central switch of network 150 through which all packet flow.

Computing device 104 includes or is in communication with a network monitoring interface for monitoring packet traffic 160 within network 150, for example, a packet sniffer, a packet analyzer, a network sensor, and/or network gateway.

Optionally, computing device 104 monitors and/or intercepts all packets transmitted over network 150. It is noted that computing device 104 may be distributed among multiple devices at different locations in network 150 to monitor and/or intercept all the packets.

Computing device 104 may be implemented as, for example one or more and/or combination of: a router, a switch, a network administration server, a group of connected devices, a client terminal, a server, a virtual server, a computing cloud, a virtual machine, a desktop computer, a thin client, a network node, a network server, and/or a mobile device (e.g., a Smartphone, a Tablet computer, a laptop computer, a wearable computer, glasses computer, and a watch computer).

Hardware processor(s) 102 of computing device 104 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 102 may include a single processor, or multiple processors (homogenous or heterogeneous) arranged for parallel processing, as clusters and/or as one or more multi core processing devices.

Memory 106 stores code instructions executable by hardware processor(s) 102, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 106 stores code 106A that implements one or more features and/or acts of the method described with reference to FIGS. 2-3 when executed by hardware processor(s) 102.

Computing device 104 may include data storage device(s) 108 for storing data, for example, one or more of: a mapping dataset for mapping static data to imaging modality type 108A, training dataset(s) 108B, code(s) for training a classifier(s) based on the training dataset(s) 108C, and code of the trained classifier(s) 108D, as described herein. Data storage device(s) 108 may be implemented as, for example, a memory, a local hard-drive, virtual storage, a removable storage unit, an optical disk, a storage device, and/or as a remote server and/or computing cloud (e.g., accessed using a network connection).

Network 150 may be implemented as, for example, a private network, a local area network, a wireless network, a wired network, the internet, a virtual network, a virtual private network, a cellular network, and/or combinations of the aforementioned. For example, network 150 is a network installed in a hospital, radiology clinic, and/or other healthcare setting, for connecting devices of the healthcare provider.

Computing device 104 and/or administration server 156 include and/or are in communication with one or more physical user interfaces 114 that include a mechanism for user interaction, for example, to enter data and/or for viewing a created connectivity graph.

Exemplary physical user interfaces 114 include, for example, one or more of, a touchscreen, a display, gesture activation devices, a keyboard, a mouse, and voice activated software using speakers and microphone.

It is noted that computing device 104 and administration server 156 may be integrated into a single computing device.

Computing device 104 and/or nodes 152 and/or nodes 154 and/or administration server 156 may include a network interface (not shown) for connecting to network 150, for example, one or more of, a network interface card, a wireless interface to connect to a wireless network, a physical interface for connecting to a cable for network connectivity, a virtual interface implemented in software, network communication software providing higher layers of network connectivity, and/or other implementations. It is noted that the network interface of computing device 104 may be integrated with network monitoring device 160.

At 202, packets transmitted over a network connecting multiple network nodes is monitored. The network is at least part of an anatomical imaging department (e.g., radiology) of a medical center (e.g., hospital, clinic, radiology center). The network includes one or more devices that are related to anatomical imaging (e.g., imaging device, PACS server, client to view PACS images), and one or more other devices that are unrelated to anatomical imaging (e.g., other server, other client devices)

The monitoring of the packets may be performed by a packet monitoring device(s) that centrally monitors all packets flowing in the network, for example, a packet sniffer, and/or packet interceptor.

Optionally, all the packets flowing through the network are monitored.

At 204, the monitored packets are analyzed to identify packets associated with a Digital Imaging and Communications in Medicine (DICOM)® protocol, for example, packets originating from an network node associated with DICOM®, packets transmitted to a destination network node associated with DICOM®, and/or packets storing DICOM® related data.

The monitored packets may be classified as being associated with DICOM® by a classifier, optionally a hierarchical classifier. The hierarchical classifier is includes multiple sub-classifiers arranged in a sequence. Output of one sub-classifier earlier in the sequence is provided as input into another sub-classifier later on in the sequence.

The packets may be classified by the hierarchical classifier in real time. For example, as each packet is sensed (e.g., sniffed, intercepted), the packet is classified by the hierarchical classifier.

The hierarchical classifier may be, for example, a binary classifier that classifies the packet(s) as being DICOM® related or not being DICOM® related.

Optionally, each sub-classifier is implemented as a logistic regression classifier. The logistic regression classifier may be a lightweight classifier (i.e., requiring relatively low processor resources, memory resources, and/or performs classification in relatively short time).

The hierarchical classifier, optionally implemented as logistic regression classifier, may be distributed across multiple computing nodes for real time computation of a large volume of packets (e.g., all packets flowing through the entire network).

The hierarchical classifier may classify each packet based on multiple extracted features, which may be extracted from the packet(s) themselves, for example, byte distribution, payload size, and interval between packets.

The lowest level sub-classifier of the hierarchical classifier may have high recall and low precision. Overall, the hierarchical architecture using the additional sub-classifiers, which are applied in a hierarchical manner, provide high recall and high precision.

A first sub-classifier (i.e., lowest level) of the sequence of sub-classifiers of the hierarchical classifier is trained on a first training dataset of packets each labeled with an indication of DICOM® data or no DICOM® data. The distribution of the packets of the first training dataset may be based on historical actual distribution of packets associated with DICOM® data with respect to other packets not associated with DICOM® data for one or more networks including imaging nodes (i.e., distribution of labels is similar to the true distribution in the wild). For example, the percentage of packets labeled with the indication of DICOM® data in the first training set is about 0.5%-1.0%. The first sub-classifier may produces very high recall (about 99.999%) and low false positive rate (FPR), but due to the high imbalance between labels, its precision is not necessarily high (about 80%).

A second sub-classifier of the sequence following the first sub-classifier (i.e., which is fed the output of the first sub-classifier) is trained on a second training dataset. In the second training dataset, the percentage of packets associated with DICOM® data is higher than the percentage of packets associated with DICOM® data of the first training dataset. The second training dataset may include packets classified as DICOM® by the first sub-classifier. The percentage of packets labeled with the indication of DICOM® data in the second training set is about 50%-90%. Better precision of the second sub-classifier is achieved, since the imbalance of the percentage of packets labeled as DICOM® is not as severe as in the first training dataset.

A third sub-classifier, or additional number of sub-classifiers of the hierarchical classifier may be provided and training on respective training dataset. Each sub-classifier of the sequence is trained on a training dataset having a percentage of packets associated with DICOM® data is higher than the percentage of packets associated with DICOM data of a training dataset used to train the previous sub-classifier of the sequence. This architecture improves precision of the hierarchical classifier.

At 206, the packets associated with the DICOM® protocol are analyzed to identify medical imaging network nodes implementing the DICOM® protocol.

At 208, a respective medical imaging type is designated for each node of the identified medical imaging network nodes. Exemplary medical imaging types include: PACS, RIS, and imaging acquisition devices, for example, MRI, x-ray, CT, and ultrasound.

Optionally, each identified medical imaging network node is designated as a medical imaging server or a medical imaging client. The packets associated with DICOM® data are analyzed to identify direction of flow of packet traffic. Traffic may be assumed to flow between identified medical imaging servers and medical imaging clients. Identified medical imaging servers and medical imaging clients are mapped according to the identified direction of flow of traffic.

Optionally, one or more network ports are determined for each respective medical imaging server.

Optionally, a name of an imaging entity is determined for each respective medical imaging client.

An exemplary process for designating the respective medical imaging type for each node of the identified medical imaging network node is described with reference to FIG. 3.

At 210, a data structure is created. The data structure defines connectivity of the medical imaging network nodes each designated with the respective medical imaging type. Server-client relationships are denoted. The medical imaging type of each node is denoted.

Optionally, the data structure is implemented as a directed graph. Nodes of the directed graph denote medical imaging nodes, including identified medical imaging servers and medical imaging clients. Edges between two certain nodes represent DICOM® associated traffic between the two nodes. Optionally, directed edges between the two certain nodes of the directed graph denote direction of packet traffic between the two nodes. For example, an outgoing edge is assigned from a client node to a server node.

Optionally, the data structure defines the network port(s) determined for each respective medical imaging server. For example, the network port(s) are stored in the node(s) of the directed graph corresponding to the respective medical imaging server(s).

Optionally, the data structure defines the name of the imaging entity association determined for each respective medical imaging client. For example, the names of the imaging entities are stored in the nodes of the directed graph corresponding to the respective medical imaging clients, for example, DICOM AE title.

Figure 4:
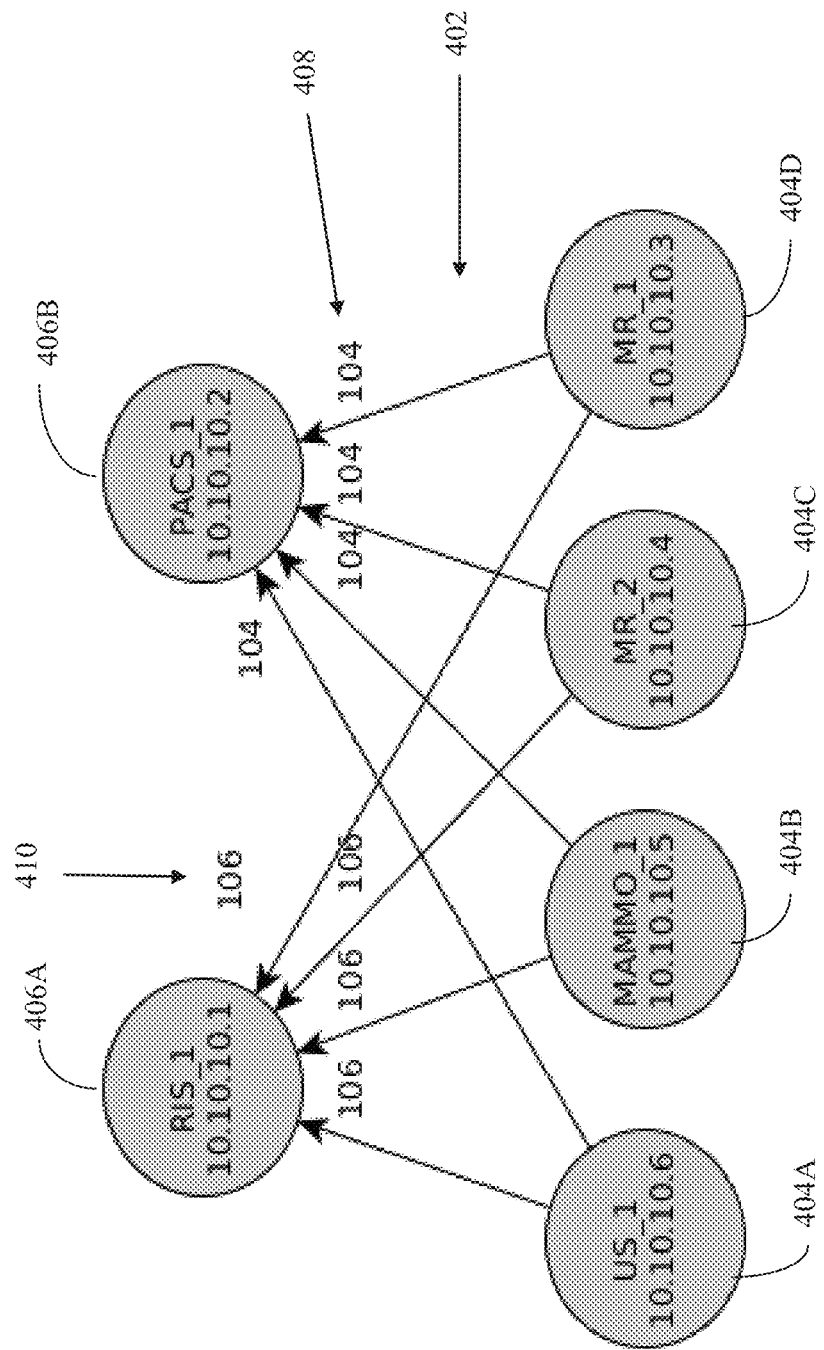
FIG. 4 is a schematic of the data structure implemented as a directed graph, in accordance with some embodiments of the present invention.

Reference is now made to FIG. 4, which is a schematic of the data structure implemented as a directed graph, in accordance with some embodiments of the present invention. Edges 402 are directed from client nodes 404A-D to server nodes 406A-B. Each server node 406 is labeled with respective server ports (e.g., 104 and 106 as shown as examples, pointed to by arrows 408 410 respectively). Within each client node 404A-D and server node 406A-B is presented the IP address of the respective node, and the DICOM AE title. For example, for client node, the IP address is 10.10.10.3, and the DICOM AE title is MR_1.

Referring now back to FIG. 2, at 212, the data structure is monitored for changes thereof, for example, by the administration server.

At 214, features described with reference to acts 202-212 are iterated.

Optionally, the data structure is used to create a behavioral model. Anomalies from the model are detected by iteratively computing an update of the data structure, and comparing the update of the data structure to the model.

At 216, the monitored changes to the data structure are analyzed to identify likelihood of activity requiring further action, for example, an anomaly, malicious activity, malware, addition of a new medical imaging network node, and removal of an existing medical imaging network node, for example, by the administration server.

At 218, instructions are generated in response to the analysis of the monitored changes, for example, by the administration server. The instructions may include automatic instructions for execution by a processor (e.g., code, script), and/or instructions for a human to manually perform. The instructions may be executed, for example, by the administration server and/or another server.

Instructions may be for containing and/or removing and/or preventing damage and/or fixing damage, for example, of: the anomaly, the malicious activity, the malware, addition of the new medical imaging network node, and removal of the existing medical imaging network node.

Figure 3:
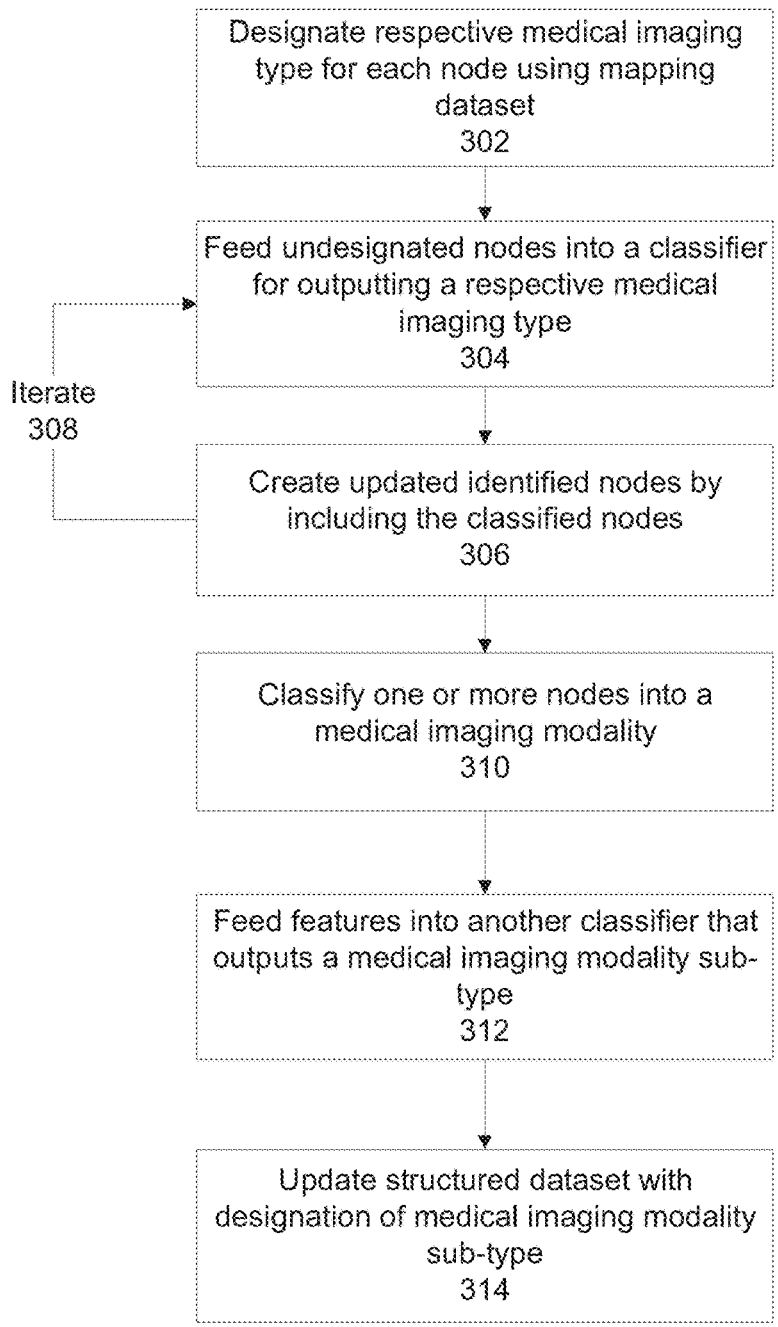
FIG. 3 is a flowchart of an exemplary process for designating the respective medical imaging type for each node of the identified medical imaging network node, in accordance with some embodiments of the present invention.

Reference is now made to FIG. 3, which is a flowchart of an exemplary process for designating the respective medical imaging type for each node of the identified medical imaging network node, in accordance with some embodiments of the present invention.

At 302, the respective medical imaging type for each node of a sub-set of the identified medical imaging network nodes is designated, optionally according to a mapping dataset. Another sub-set of the identified medical imaging network nodes are undesignated with medical imaging type.

The mapping dataset may map between one static signature(s) extracted from one or more packets and one of multiple candidate medical imaging types. Exemplary static signatures includes: DICOM implementation UID, and DICOM implementation version name. The static signatures may be values that are sent by the DICOM node during the association process, and may be used to identify the type of the node. For example, a GE Centricity PACS version 2.1 is identified by implementation UID 1.2.840.113619.6.94 and implementation version name CENTRICITY 2.1. In operation, when an A-ASSOCIATE DICOM message is detected from a node with the previously cited values, the node may be designated as a PACS.

The undesignated nodes may remain undesignated due to lack of matching their static signature(s) to medical imaging type by the mapping dataset.

At 304, node(s) of the other sub-set, which includes the undesignated medical imaging nodes, are fed into a classifier, which outputs a classification of a respective medical imaging type. Features are extracted from packets associated with the undesignated medical imaging node are fed into the classifier.

It is noted that the classifier may be used to determine the classification of medical imaging type for nodes which have not been classified using the static signatures by the mapping dataset described with reference to act 302.

The classifier may be implemented as, for example, an XGBoost classifier.

The features may be dynamically extracted according to packets captured by a sliding window defining a time interval, for example, the last predefined number of minutes of activity of the respective node.

Optionally, the classifier is trained according to a training dataset that includes tags indicative of the medical imaging type for each node of the identified medical imaging nodes, and associated features extracted from packets associated with each respective medical imaging network node. The associated features may include local features and/or relationship features. Local features may be features of the respective node, independent of medical imaging types of neighboring nodes (i.e., independent of labels of neighboring nodes). Exemplary local features include: overall number of C-STORE messages sent by the respective node, and/or overall number of other nodes with which the respective node communicates with. Relational features may be features that are dependent on the medical imaging types of neighboring nodes. Exemplary relational features include number of C-STORE messages sent by the respective node to a PACS. For example, to calculate the number of C-STORE messages sent from the node to a PACS, the label of the neighboring nodes may be required. Each C-STORE message is distinguished to determine whether the respective C-STORE message was sent to a PACS or to a different type of node, for example a workstation or a migration service such as a burner.

Optionally, the classifier is used to classify some of the unclassified nodes. Other unclassified remain unclassified.

At 306, an updated sub-set of identified medical imaging network nodes is created by including the classified medical imaging type of each node classified by the classifier.

At 308, features described with reference to acts 304-306 are iterated. The updated sub-set of identified medical imaging network nodes and associated features dynamically extracted from packets associated with each respective classified node, which are obtained during a current iteration, are fed into the classifier during the next iteration, until a stop condition is met. At each iteration additional medical imaging network nodes which are undesignated with medical imaging type are classified by the classifier. At each iteration, some unclassified nodes may remain unclassified. The stop condition may be when no undesignated nodes remain, and/or when the classification of the nodes (e.g., all nodes) stabiles (i.e., unchanged between iterations), and/or when a predefined number of iterations is reached, and/or where a probability of accuracy of classification outputted by the classifier is above a threshold.

Optionally, at each iteration, nodes previously classified by the classifier in an earlier iteration are re-fed into the classifier (i.e., the extracted features associated with the nodes are re-fed) for reclassification of the nodes. Optionally, all previously classified nodes are re-classified by the classifier. The re-classification may be performed, since relationship extracted features which depend on other nodes may change during the iterations. The updated relationship features may result in a re-classification of a previously classified node into another classification. For example, a certain node is classified into a first medical imaging type (e.g., server) in a first iteration, without using relational features, when no classified neighboring nodes are available. During the same iteration, at least some of the unclassified neighboring nodes are classified. During the next iteration, relational features are extracted from the now classified neighbors, and used to re-classify the certain node, from the previous server classification to a current client classification.

At 310, the medical imaging type of one or more of the medical imaging network nodes is classified into a medical imaging modality.

In features 302-308, a certain node may be classified into a broad category of a medical imaging modality, or another category which is not a medical imaging category. The broad category of the medical imaging modality does not necessarily define the actual type of medical imaging modality, for example, does not specify whether the node is an x-ray machine, a CT scanner, an MRI machine, or an ultrasound machine.

Another set of features is extracted based on packets associated with each respective medical imaging network node designated and/or classified as medical imaging modality.

At 312, another set of features is fed into another classifier that outputs a medical imaging modality sub-type of multiple candidate medical imaging modality sub-types.

The other classifier may be trained on a training dataset of labeled features based on static signatures. The other set of features includes, for example, DICOM SOP classes that the respective node sends, for example, the overall number of messages with SOP class 1.2.840.10008.5.1.4.1.1.3.1, which is the SOP class for "Ultrasound Multiframe Image Storage".

The other classifier may be different than the classifier described with reference to 304. The other set of features of 312 may be different, the same, and/or overlap with the set of features described with reference to 304. The separation between the classifies described with reference to 304 and the classifier described with reference to act 312 may reduce the dimensionality of each classifier, and/or use different features in each classifier for highest accuracy by the respective classifier, which improves overall computational efficiency and/or classification accuracy.

At 314, each respective medical imaging network node classified and/or designated as medical imaging type is designated according to the respective classified medical imaging modality sub-type. Optionally, the structured dataset (e.g., directed graph) is updated with the designation, for example, the node of the directed graph corresponding to the medical imaging type is updated with the classified medical imaging modality sub-type.

Reference is now made to FIGS. 5A-D, which are schematics depicting the iterative process of identifying the medical imaging type for unclassified nodes, in accordance with some embodiments of the invention. The iterative process of identifying the medical imaging type for unclassified nodes is described with reference to acts 302-314 of FIG. 3. FIGS. 5A-D depict the data structure described herein, implemented as a directed graph, that defines connectivity of the identified medical imaging network nodes and corresponding classified or unclassified medical imaging type.

Figure 5A:
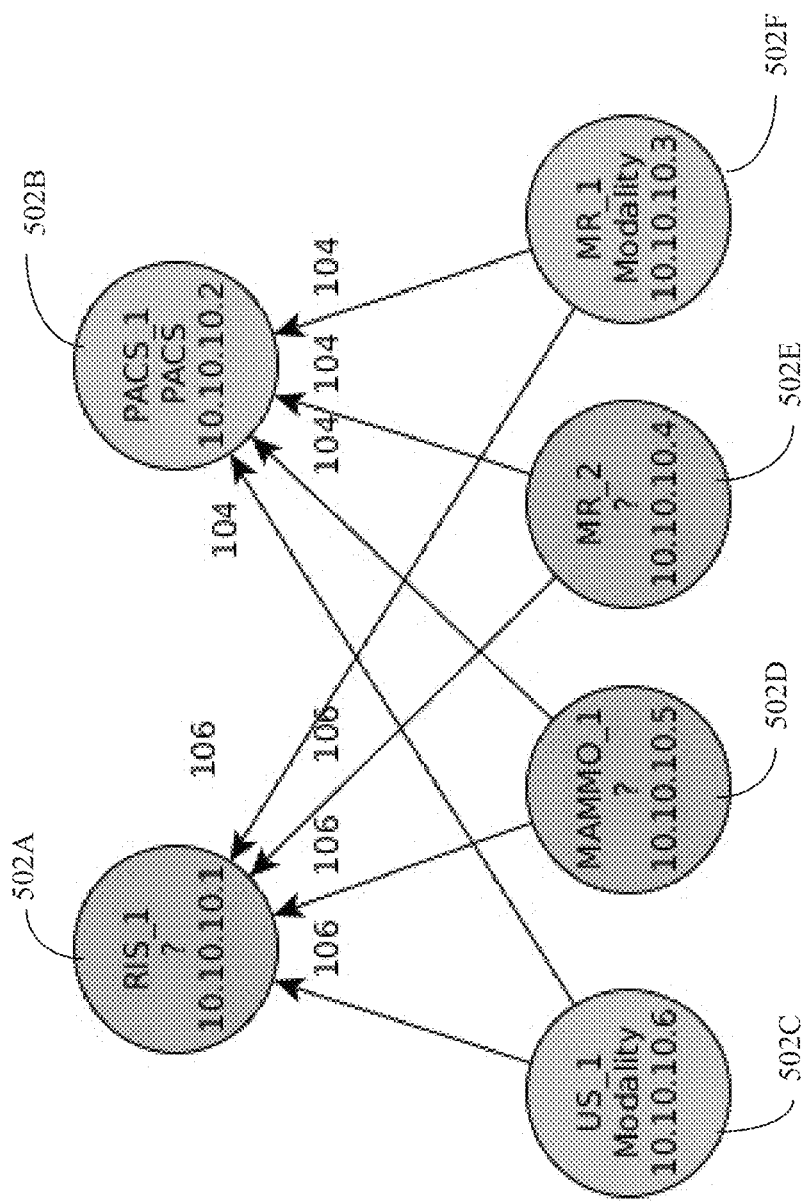
FIGS. 5A-5D are schematics depicting the iterative process of identifying the medical imaging type for unclassified nodes, in accordance with some embodiments of the invention.

FIG. 5A depicts the state of the directed graph data structure after feature 302 of FIG. 3. Nodes 502B, 502C, and 502F are classified into their respective medical imaging types (i.e., respectively: PACS, Modality, Modality), optionally using the mapping dataset based on static signatures, as described with reference to feature 302 of FIG. 3. Nodes 502A, 502D, and 502E remain undesignated (i.e., unclassified).

Figure 5B:
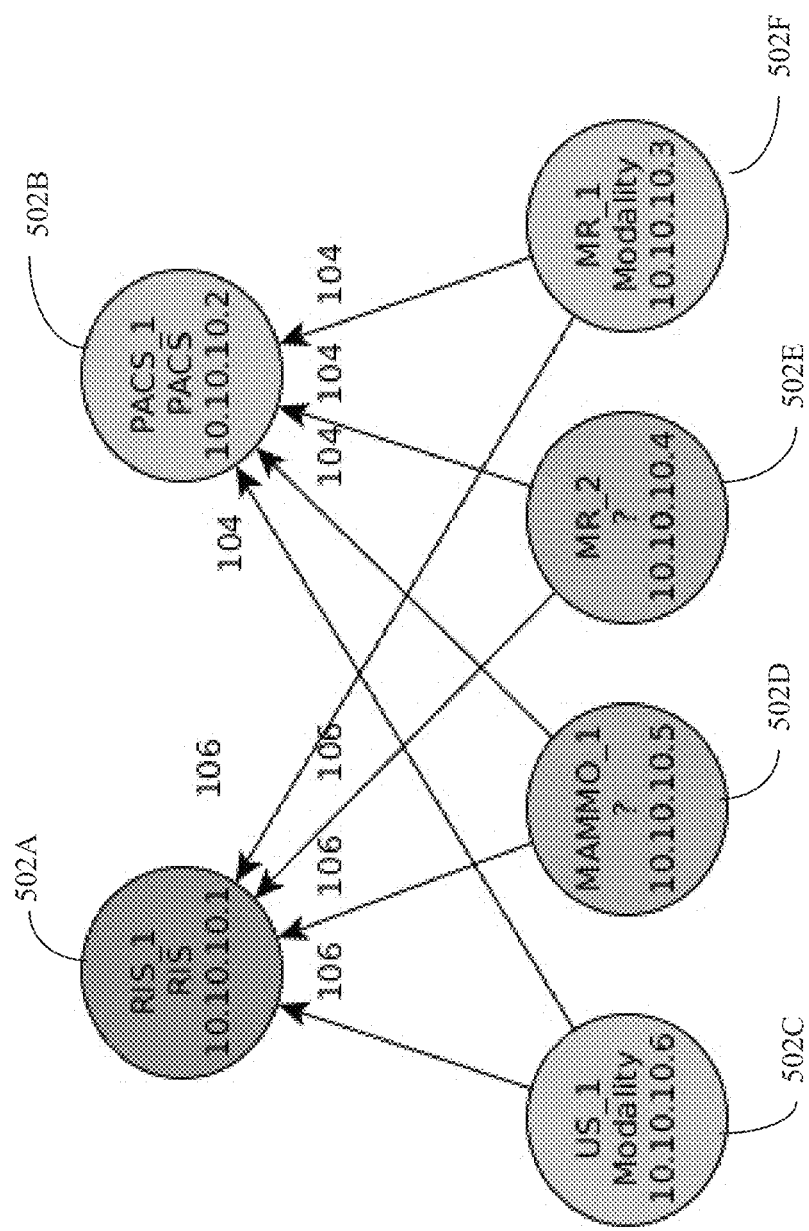

FIG. 5B depicts the state of the directed graph data structure of FIG. 5A after a first iteration, i.e., features 304-306 of FIG. 3. Node 502A, called RIS_1, which was previously undesignated after feature 302 as shown in FIG. 5A, is classified by the classifier into the category RIS (Radiologist Information System), as described with reference to feature 304. Nodes 502D and 502E remain unclassified. FIG. 5B depicts the update directed graph data structure as described with reference to feature 308 of FIG. 3.

Figure 5C:
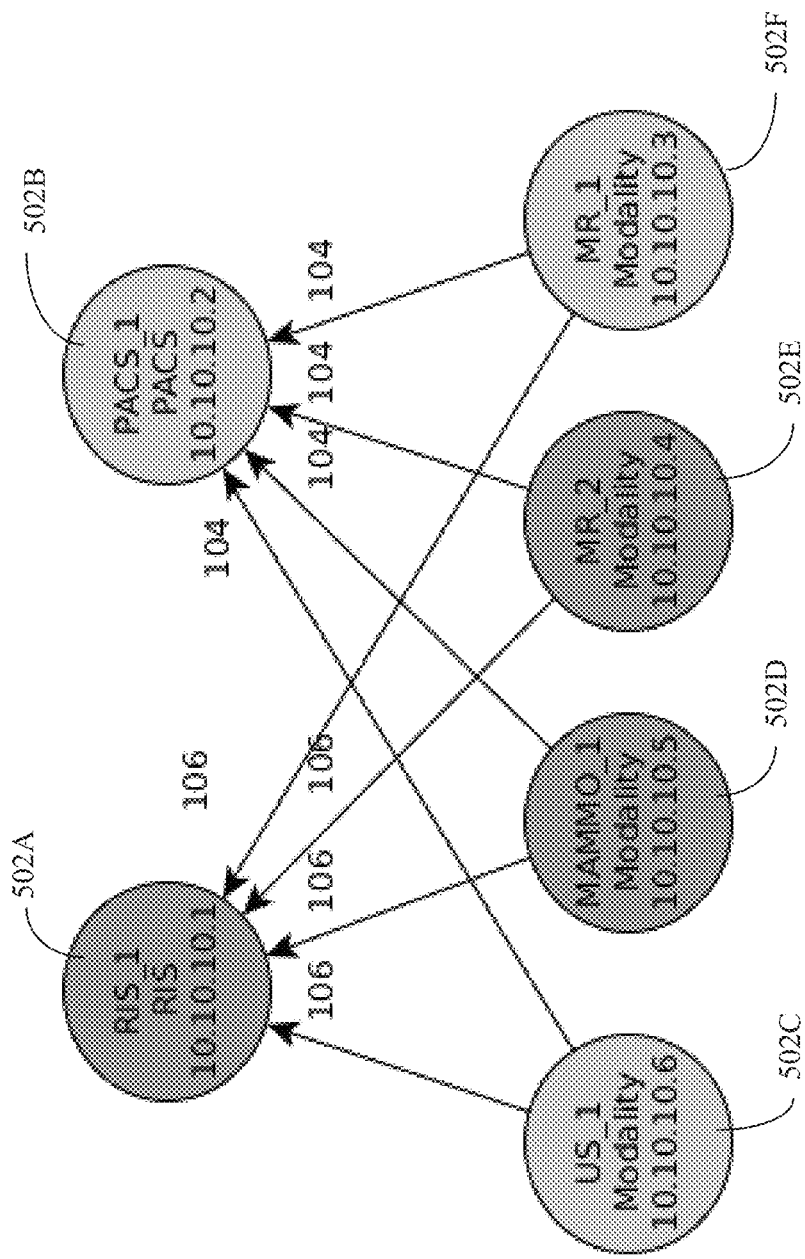

FIG. 5C depicts the state of the directed graph data structure of FIG. 5A after a second iteration, i.e., 304-308 of FIG. 3. Nodes 502D and 502E. which were previously undesignated after the first iteration (i.e., features 304-306 of FIG. 3, as shown in FIG. 5B) are classified by the classifier during the second iteration. The classifier is able to classify nodes 502D and 502E based on relational features that include Node 502A that was classified in the previous iteration.

Figure 5D:
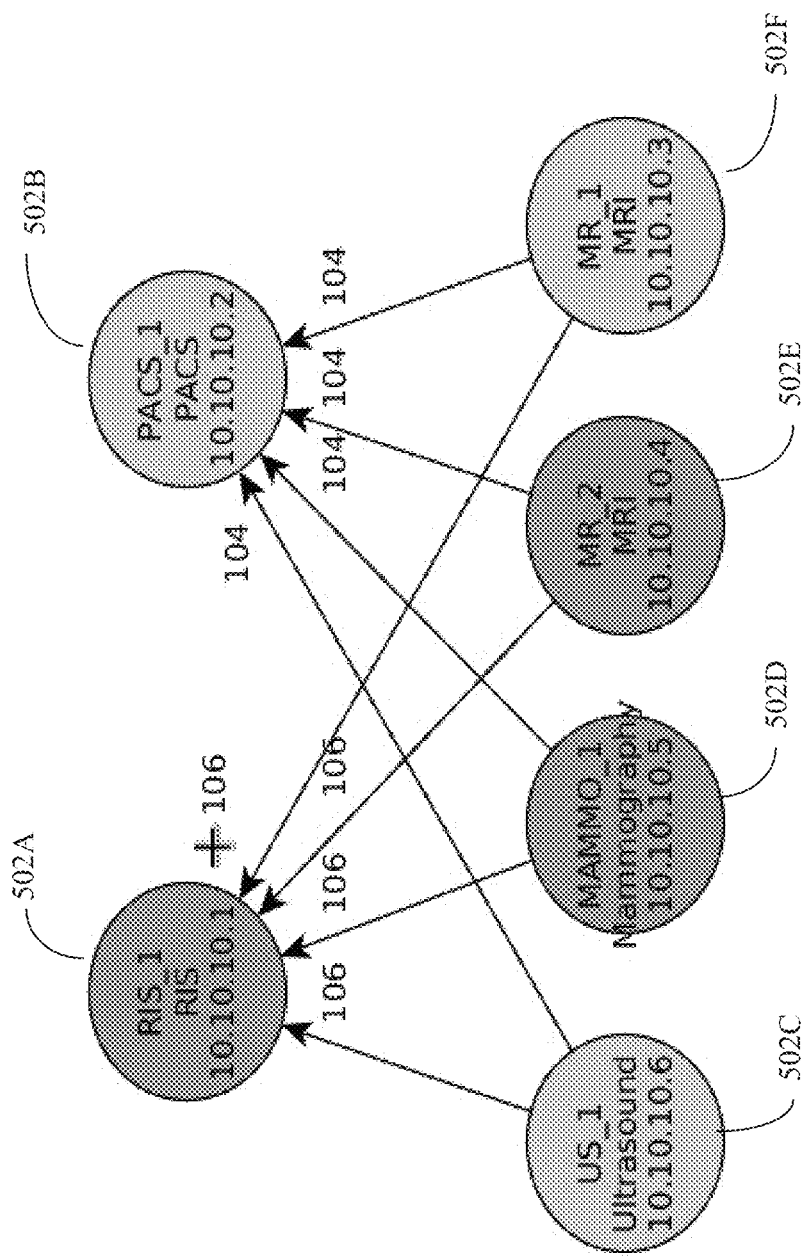

FIG. 5D depicts the state of the directed graph data structure of FIG. 5C, after features 310-314 of FIG. 3. Nodes 502C-F, which have been previously classified into the broad category of Modality are further classified into subcategories indicative of the modality type, respectively, ultrasound, ultrasound, MRI, and MRI.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant network nodes will be developed and the scope of the term node is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A system for computing connectivity of medical imaging network nodes, comprising:
at least one hardware processor executing codes for:
monitoring packets transmitted over a network connecting a plurality of network nodes;
analyzing the monitored packets to identify packets associated with a Digital Imaging and Communications in Medicine (DICOM) protocol;
analyzing the packets associated with the DICOM protocol to identify medical imaging network nodes implementing the DICOM protocol;
designating a respective medical imaging type for each node of the medical imaging network nodes;
computing a data structure storing connectivity of the medical imaging network nodes each designated with the respective medical imaging type; and
designating each identified medical imaging network node as a medical imaging server or a medical imaging client;
analyzing the packets associated with DICOM data to identify direction of flow of traffic and between identified medical imaging servers and medical imaging clients; and
mapping identified medical imaging servers and medical imaging clients according to the identified direction of flow of traffic,
wherein the data structure stores the identified medical imaging servers and medical imaging clients according to the identified direction of traffic flow.

2. The system of claim 1, further comprising code for monitoring for changes to the data structure.

3. The system of claim 2, wherein the data structure is used as a behavioral model, and wherein the monitoring for changes to the data structure comprises iterating the monitoring packets, the analyzing the monitored packets, the analyzing the packets associated with the DICOM protocol, the designating the respective medical imaging type, and wherein computing comprises an update of the data structure, and comparing the update of the data structure to the behavioral model.

4. The system of claim 3, further comprising code for analyzing the monitored changes to the data structure to identify likelihood of at least one of: an anomaly, malicious activity, malware, addition of a new medical imaging network node, and removal of an existing medical imaging network node.

5. The system of claim 4, further comprising generating instructions for containing or removing or preventing damage from or fixing damage due to the at least one of: an anomaly, malicious activity, malware, addition of a new medical imaging network node, and removal of an existing medical imaging network node.

6. The system of claim 1, further comprising code for determining at least one network port for each respective medical imaging server and storing the determined at least one network port in association with each respective medical imaging server, and code for determining a name of an imaging entity for each respective medical imaging client and storing the determined name of the imaging entity in association with each respective medical imaging client.

7. The system of claim 1, wherein the analyzing the monitored packets to identify packets associated with the DICOM protocol comprises classifying the monitored packets by a hierarchical classifier comprising a plurality of sub-classifiers arranged in a sequence, wherein output of one sub-classifier earlier in the sequence is provided as input into another sub-classifier later on in the sequence.

8. The system of claim 7, wherein each sub-classifier is implemented as a logistic regression classifier.

9. The system of claim 7, wherein the hierarchical classifier is distributed across a plurality of computing nodes for real time computation of a large volume of packets.

10. The system of claim 7, wherein the hierarchical classifier classifies each packet based on a plurality of extracted features, including: byte distribution, payload size, and interval between packets.

11. The system of claim 1, wherein the data structure is a directed graph, wherein nodes of the directed graph denote medical imaging nodes including medical imaging servers and medical imaging clients, and directed edges between nodes of the directed graph denote direction of traffic.

12. The system of claim 1, wherein the monitoring packets is performed by a packet monitoring device that centrally monitors all packets flowing in the network.

13. A system for computing connectivity of medical imaging network nodes, comprising:
at least one hardware processor executing codes for:
monitoring packets transmitted over a network connecting a plurality of network nodes;
analyzing the monitored packets to identify packets associated with a Digital Imaging and Communications in Medicine (DICOM) protocol;
analyzing the packets associated with the DICOM protocol to identify medical imaging network nodes implementing the DICOM protocol;
designating a respective medical imaging type for each node of the medical imaging network nodes;
computing a data structure storing connectivity of the medical imaging network nodes each designated with the respective medical imaging type;
designating the respective medical imaging type for each node of a sub-set of the identified medical imaging network nodes according to a mapping dataset, wherein another sub-set of the identified medical imaging network nodes are undesignated with medical imaging type; and
classifying, by a classifier, at least one node of the another sub-set of undesignated medical imaging nodes, into a respective medical imaging type;
creating an updated sub-set of identified medical imaging network nodes by including the classified medical imaging type of each node classified by the classifier; and
iterating the classifying and the creating, by feeding the updated sub-set of identified medical imaging network nodes and associated features dynamically extracted from packets associated with each respective classified node, obtained during a previous iteration, into the classifier during a current iteration, until a stop condition is met.

14. The system of claim 13, wherein the classifier is trained according to a training dataset including tags indicative of a medical imaging type of each node of identified medical imaging nodes and associated features extracted from packets associated with each respective medical imaging network node.

15. The system according to claim 13, wherein the mapping dataset maps between at least one static signature extracted from a respective packet and one of a plurality of medical imaging types.

16. The system according to claim 15, wherein the static signature includes at least one of: DICOM implementation UID and DICOM implementation version name.

17. The system according to claim 13, wherein the associated features include at least one of: local features of the respective node independent of medical imaging types of neighboring nodes, and relational features dependent on medical imaging types of neighboring nodes.

18. The system according to claim 17, wherein the local features include at least one of: overall number of C-STORE messages sent by the respective node, and overall number of other nodes with which the respective node communicates with, wherein the relational features include at least one of: number of C-STORE messages sent by the respective node to a PACS.

19. The system according to claim 13, wherein the associated features are dynamically extracted according to packets captured by a sliding window defining a time interval.

20. The system according to claim 13, wherein the medical imaging type of at least one of the medical imaging network nodes is a medical imaging modality, and further comprising code for:
    extracting at least one feature from packets associated with each respective medical imaging network node designated and/or classified as medical imaging modality;
    classifying the at least one feature by another classifier, into a medical imaging modality sub-type of a plurality of medical imaging modality sub-types; and
    designating each respective medical imaging network node classified and/or designated as medical imaging type into the classified medical imaging modality sub-type.

21. The system according to claim 20, wherein the at least one feature includes DICOM SOP classes.

22. A system for computing connectivity of medical imaging network nodes, comprising:
    at least one hardware processor executing codes for:
        monitoring packets transmitted over a network connecting a plurality of network nodes;
        analyzing the monitored packets to identify packets associated with a Digital Imaging and Communications in Medicine (DICOM) protocol;
        analyzing the packets associated with the DICOM protocol to identify medical imaging network nodes implementing the DICOM protocol;
        designating a respective medical imaging type for each node of the medical imaging network nodes;
        computing a data structure storing connectivity of the medical imaging network nodes each designated with the respective medical imaging type;
    wherein the analyzing the monitored packets to identify packets associated with the DICOM protocol comprises classifying the monitored packets by a hierarchical classifier comprising a plurality of sub-classifiers arranged in a sequence, wherein output of one sub-classifier earlier in the sequence is provided as input into another sub-classifier later on in the sequence;
    wherein a first sub-classifier of the sequence is trained on a first training dataset of packets each labeled with an indication of DICOM data or no DICOM data, wherein the distribution of the packets of the first training dataset is based on historical actual distribution of packets associated with DICOM data with respect to other packets not associated with DICOM data for a plurality of sample networks including imaging nodes.

23. The system of claim 22, wherein the percentage of packets labeled with the indication of DICOM data in the first training set is about 0.5%-1.0%.

24. The system of claim 22, wherein a second sub-classifier of the sequence following the first sub-classifier is trained on a second training dataset wherein a percentage of packets associated with DICOM data is higher than the percentage of packets associated with DICOM data of the first training dataset.

25. The system of claim 24, wherein the percentage of packets labeled with the indication of DICOM data in the second training set is about 50%-90%.

26. The system of claim 24, wherein for a plurality of sub-classifiers of the hierarchical classifier, each sub-classifier of the sequence is trained on a training dataset wherein a percentage of packets associated with DICOM data is higher than the percentage of packets associated with DICOM data of a training dataset used to train the previous sub-classifier of the sequence.

27. Method of computing connectivity of medical imaging network nodes, comprising:
    monitoring packets transmitted over a network connecting a plurality of network nodes;
    analyzing the monitored packets to identify packets associated with a Digital Imaging and Communications in Medicine (DICOM) protocol;
    analyzing the packets associated with the DICOM protocol to identify medical imaging network nodes implementing the DICOM protocol;
    designating a respective imaging type for each node of the medical imaging network nodes;
    computing a data structure storing connectivity of the medical imaging network nodes each designated with the respective imaging type;
    designating each identified medical imaging network node as a medical imaging server or a medical imaging client;
    analyzing the packets associated with DICOM data to identify direction of flow of traffic and between identified medical imaging servers and medical imaging clients; and
    mapping identified medical imaging servers and medical imaging clients according to the identified direction of flow of traffic;
    wherein the data structure stores the identified medical imaging servers and medical imaging clients according to the identified direction of traffic flow.

28. A computer program product for computing connectivity of medical imaging network nodes, comprising:
    a non-transitory memory storing thereon code for execution by at least one hardware process, the code including instructions for:
        monitoring packets transmitted over a network connecting a plurality of network nodes;
        analyzing the monitored packets to identify packets associated with a Digital Imaging and Communications in Medicine (DICOM) protocol;
        analyzing the packets associated with the DICOM protocol to identify medical imaging network nodes implementing the DICOM protocol;
        designating a respective imaging type for each node of the medical imaging network nodes;
        computing a data structure storing connectivity of the medical imaging network nodes each designated with the respective imaging type;

designating each identified medical imaging network node as a medical imaging server or a medical imaging client;

analyzing the packets associated with DICOM data to identify direction of flow of traffic and between identified medical imaging servers and medical imaging clients; and mapping identified medical imaging servers and medical imaging clients according to the identified direction of flow of traffic;

wherein the data structure stores the identified medical imaging servers and medical imaging clients according to the identified direction of traffic flow.

\* \* \* \* \*